US011705225B2

(12) United States Patent
Bauer et al.

(10) Patent No.: US 11,705,225 B2
(45) Date of Patent: *Jul. 18, 2023

(54) SYSTEM AND A METHOD FOR MANAGING INFORMATION RELATING TO SAMPLE TEST REQUESTS WITHIN A LABORATORY ENVIRONMENT

(71) Applicant: Roche Diagnostics Operations, Inc., Indianapolis, IN (US)

(72) Inventors: Ralf Bauer, Frankenthal (DE); Werner Schönenberger, Sins (CH); Roger Iten, Sins (CH)

(73) Assignee: Rodie Diagnostics Operations, Inc., Indianapolis, IN (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/534,918

(22) Filed: Nov. 24, 2021

(65) Prior Publication Data

US 2022/0084637 A1 Mar. 17, 2022

Related U.S. Application Data

(60) Division of application No. 15/989,976, filed on May 25, 2018, now Pat. No. 11,211,152, which is a (Continued)

(30) Foreign Application Priority Data

Jun. 1, 2006 (EP) ..................................... 06011422

(51) Int. Cl.
*G01N 35/10* (2006.01)
*G01N 35/00* (2006.01)
*G16H 10/40* (2018.01)

(52) U.S. Cl.
CPC ............ *G16H 10/40* (2018.01); *Y10T 436/11* (2015.01)

(58) Field of Classification Search
None
See application file for complete search history.

(56) References Cited

U.S. PATENT DOCUMENTS 5,841,975 A 11/1998 Layne et al.
6,581,012 B1 6/2003 Aryev et al.
(Continued)

FOREIGN PATENT DOCUMENTS

WO 9826365 A1 6/1998
WO 0193762 A2 12/2001
(Continued)

OTHER PUBLICATIONS

European Patent Office Search Report dated Mar. 9, 2007 in reference to European Patent Application No. PCT/EP2007/004581 filed May 23, 2007.

*Primary Examiner* — P. Kathryn Wright
(74) *Attorney, Agent, or Firm* — Thomas E. Lees, LLC

(57) ABSTRACT

A system and method for managing information relating to requests for a number of tests to be made of at least one sample within a laboratory environment are disclosed. The system may include a sample reception unit, a pre-analytical unit to scan, sort and/or aliquot the sample on request according to respective test requirements included within a respective sample order, an analytical unit to run at least one test on a sorted and/or aliquoted sample, and at least one decision unit. The decision unit acts as a connecting component for interconnecting the sample reception unit, the pre-analytical unit and the analytical unit as both an intermediary and coordinator such that tests can be performed via a recursive workflow until the sample is completely measured. The decision unit is further configured to collate the
(Continued)

test results appropriately with the sample and to give a respective report towards a host component.

4 Claims, 5 Drawing Sheets

Related U.S. Application Data continuation of application No. 12/277,681, filed on Nov. 25, 2008, now abandoned, which is a continuation of application No. PCT/EP2007/004581, filed on May 23, 2007.

(56) References Cited

U.S. PATENT DOCUMENTS

| | | | |
|---|---|---|---|
| 6,721,615 | B2 | 4/2004 | Fava et al. |
| 2004/0033501 | A1 | 2/2004 | Lappe et al. |
| 2007/0282476 | A1* | 12/2007 | Song .................. G16H 40/20 |
| | | | 705/7.18 |

FOREIGN PATENT DOCUMENTS

| | | |
|---|---|---|
| WO | 03065033 A2 | 8/2003 |
| WO | 2007137750 A1 | 12/2007 |

* cited by examiner

Figure 5

Sample 123 with test request T1/T2/T3/T4
Query 1: Hamilton->PSM for sample 123
Answer: PSM->Hamilton                    sample ID 123 with test requests T1/T2/T3/T4
Result Record Hamilton->PSM for sample 123:  sample ID 123 T1;R-ID/R-Pos/123

Query 2: Hamilton->PSM for sample 123
Answer: PSM->Hamilton                    sample ID 123 with test requests T2/T3/T4
Result Record Hamilton->PSM for sample 123:  sample ID 123 T2;R-ID/R-Pos/123

Query 3: Hamilton->PSM for sample 123
Answer: PSM->Hamilton                    sample ID 123 with test requests T3/T4
Result Record Hamilton->PSM for sample 123:  sample ID 123 T3,T4;R-ID/R-Pos/123

Query 4: Hamilton->PSM for sample 123
Answer: PSM->Hamilton                    sample ID 123 no test requests
                                         Empty record is sent in this case

SYSTEM AND A METHOD FOR MANAGING INFORMATION RELATING TO SAMPLE TEST REQUESTS WITHIN A LABORATORY ENVIRONMENT

CROSS REFERENCE TO RELATED APPLICATIONS

This application is a divisional of U.S. application Ser. No. 15/989,976 filed May 25, 2018, which is a continuation of U.S. application Ser. No. 12/277,681, filed Nov. 25, 2008, which is a continuation of International Application No. PCT/EP2007/004581, filed 23 May 2007, which claims priority to EP Application No. 06011422.0, filed Jun. 1, 2006, which are herein incorporated by reference.

FIELD OF THE INVENTION

The present invention relates generally to data management within a laboratory environment and more particularly, to a system and a method for managing information relating to requests for a number of tests to be made on at least one sample within a laboratory environment.

BACKGROUND OF THE INVENTION

In some current laboratory environments, an increased amount of samples have to be handled. They have to be tested with respect to a broad range of different properties. Those laboratories have particularly a lot of different instruments for automated sample preparation and for automated analysis. Those laboratory processes include pre-analytical, analytical and post-analytical steps and require at the same time powerful data management functions. Therefore, it is a pre-requisite for optimizing a complete laboratory process to combine those pre-analytical, analytical and post-analytical decisions with data management functions. Moreover, it would be desirable to provide one uniform backbone to realize advanced sample workflows in a uniform manner to increase laboratory efficiency and to deliver high quality results. Simultaneously, it would be desirable, that the complexity of such laboratory processes is reduced, while improving quality and providing a satisfying work environment.

SUMMARY OF THE INVENTION

Therefore, the present disclosure provides a system and a method, which allow small to very large laboratory sites, as for example molecular diagnostic sites, to realize customer solutions combining fully computer aided sample handling functions with data management decisions.

Those laboratory sites have, as already mentioned, typically one or more units for sample preparation and one or more units for analysis, e.g. in case of molecular diagnostic laboratories for amplification and detection.

According to one embodiment, a system for managing information relating to requests for a number of tests to be made on at least one sample within a laboratory environment is disclosed. The system comprises at least one pre-analytical unit, which is configured to scan the at least one sample and to sort and/or aliquot the at least one sample on request according to respective test requirements, at least one analytical unit configured to run at least one test of the number of tests on the appropriately sorted and/or aliquoted sample and a decision unit enabling at least one host component to access the system and to submit the sample order, and acting as connecting component for interconnecting the at least one pre-analytical unit and the at least one analytical unit and as intermediary and coordinator in communication between those units, such that the number of tests can be performed via a workflow, such as via a recursive workflow, coordinated by the decision unit until a pre-given stopping criterion is fulfilled, such as until the sample is completely measured, the decision unit being further configured to collate the test results appropriately with the sample and to give a respective report towards the at least one host component.

In a further embodiment, a decision unit for managing information relating to requests for a number of tests to be made on at least one sample in a system within a laboratory environment is disclosed. The system within the laboratory environment comprises at least one pre-analytical unit and at least one analytical unit. The decision unit enables at least one host component to access the system and to submit a sample order for the at least one sample. Furthermore, the decision unit acts as a connection component for interconnecting the at least one pre-analytical unit and the at least one analytical unit and as intermediary and coordinator in communication between those units, such that the number of tests can be performed via a workflow, such as via a recursive workflow, coordinated by the decision unit, until a pre-given criterion is fulfilled, such as until the sample is completely measured. The decision unit is further configured to correlate the test results appropriately with the sample and to give a respective report towards the at least one host component.

A further embodiment refers to a method for managing information related to requests for a number of tests to be made on at least one sample in a system within a laboratory environment, the system within the laboratory environment comprising at least one pre-analytical unit, at least one analytical unit and one decision unit. The method comprises: receiving the sample, transporting the sample to the at least one pre-analytical unit, identifying the sample and assigning the sample to a sample order, processing the sample according to the sample order by a dynamically adaptable coordinated interaction of the at least one pre-analytical unit and the at least one analytical unit, and giving a report about the processing to at least one host component, wherein the coordination between the respective units is managed by the decision unit acting as intermediary and coordinator in communication between the respective units and the report is given by the decision unit acting as consolidating front end related to the at least one host component.

The present invention also relates in one embodiment to a computer-readable medium with a computer program stored thereon, the computer program comprising a program code, which is suitable for carrying out a method according to the disclosure when the computer program is run on a computer, such as on a computer integrated within a system and/or a decision unit according to the present disclosure.

Further features and embodiments will become apparent from the description and the accompanying drawings.

BRIEF DESCRIPTION OF THE DRAWINGS

FIG. 5 shows a schematic simple recursive workflow realizable by an embodiment of the system according to the present disclosure.

DETAILED DISCUSSION

Figure 1:
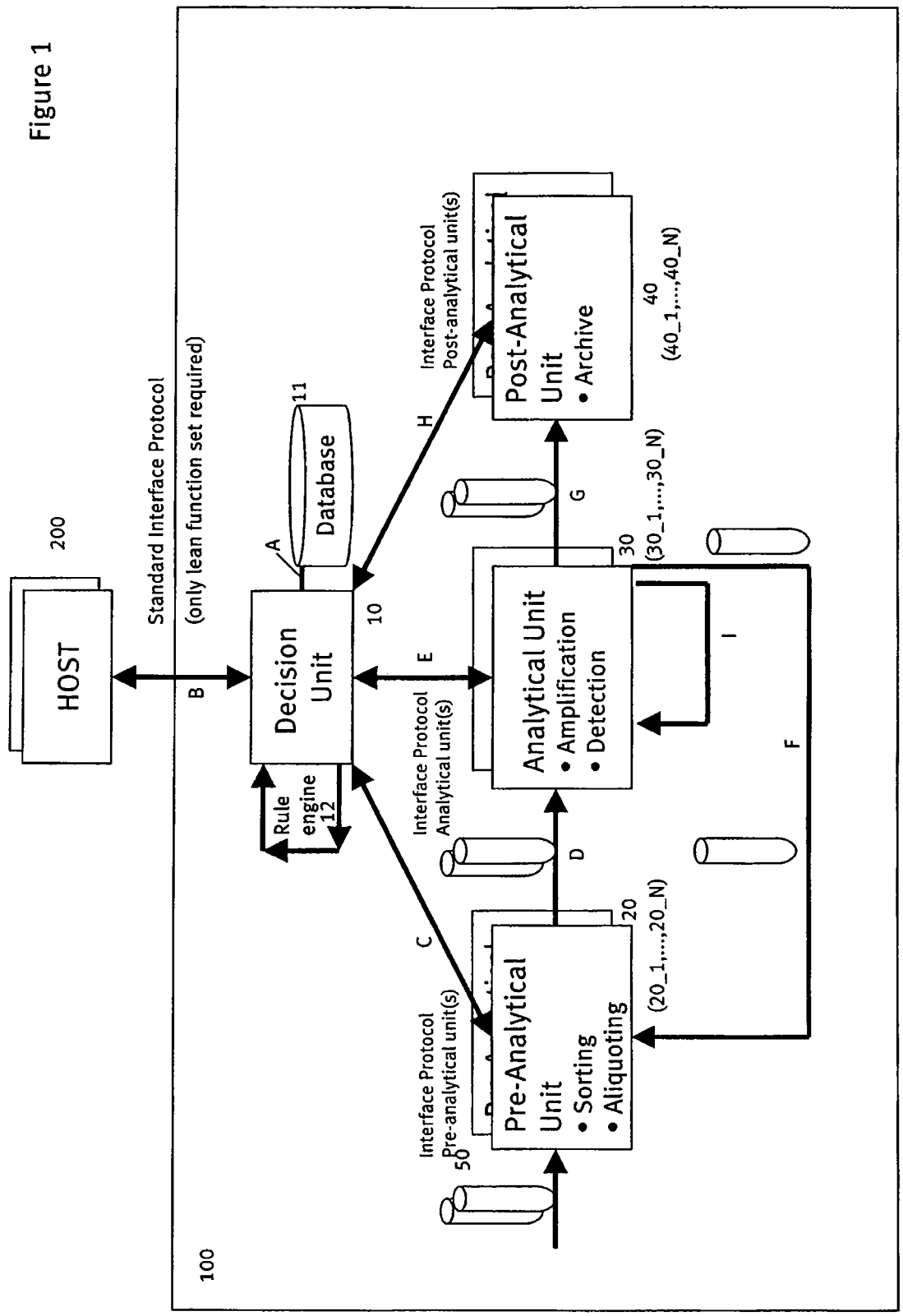
FIG. 1 shows a schematic block diagram of a possible embodiment of a system according to the present disclosure.

For purposes of clarity, the present discussion refers to an abstract example of a system. However, the method and the system of the present disclosure may operate with a wide variety of types of systems including networks and communication systems dramatically different from the specific example as illustrated in the drawings.

It should be understood that while the following is described in terms of a specific system, that there are applications in a variety of communication systems, such as advanced medical laboratory systems, advanced laboratory networks or any other communication system that would benefit from the system or the method according to the present disclosure. It is intended that the system as used in the specification and claims is suitable to be used in any communication system unless the context requires otherwise.

An implementation is schematically illustrated in the drawings by way of an example embodiment and is explained in detail with reference to the drawings. It is understood that the description is in no way limiting on the scope of the present disclosure and is merely an illustration of an example implementation.

In the following, similar components are referred to by equal reference numbers.

FIG. 1 shows a block diagram of an embodiment of the system according to the present disclosure. The system 100 comprises a decision unit 10, at least one pre-analytical unit 20, at least one analytical unit 30 and at least one post-analytical unit 40. The possibility of a multiplicity of the respective units is indicated by an appropriate enumeration and by successively arranged boxes, respectively. The decision unit 10 is further connected with a database 11 as indicated by link A. The database 11 can also be integrated within the decision unit 10. The decision unit 10 is connected, as indicated by link B, with at least one or more host components 200. Via standard host interface protocols, e.g. ASTM or HL7, the decision unit 10 can communicate with at least one host component 200 with a standard function set. No specific logic has to be realized in the host system. Therefore, it can be integrated fast, easy and with low risk.

During runtime of the system 100, a sample order comprising a sample-ID and sample test requests can be downloaded from at least one host component 200 to the decision unit 10 of the system 100 via standard interface protocols. Sample test request information and sample information, optionally including other sample and patient demographic information, which is included in the sample order, is stored in the local database 11 of the decision unit 10. A sample in form of a sample tube 50 is arriving, as indicated on the left side of FIG. 1, in the pre-analytical unit 20. A sample scan is preformed by the pre-analytical unit 20 which is sent via link C to the decision unit 10.

The decision unit 10 is downloading to the pre-analytical unit 20 via link C sample information, i.e. an appropriate target information or pending test requests which are included in the sample order. Depending on the downloaded sample information, e.g. target or pending tests, the at least one pre-analytical unit 20 is performing the required action, i.e. sorting or aliquoting the sample tube 50, and putting the sample tube 50 into an appropriate target. The pre-analytic sorting/aliquoting information is uploaded (e.g. in form of an extended sample order) via link C to the decision unit 10. The sorted aliquoted sample tube 50 is put via link D on the analytical unit 30.

Either in batch or in query mode the analytical unit 30 is asking via link E for the appropriate test request information from the decision unit 10. The decision unit 10 is downloading via link E the extended sample order including the corresponding information to the analytical unit 30. After the corresponding test(s) has (have) been done by the analytical unit 30, the test results are uploaded from the analytical unit 30 via link E to the decision unit 10.

The decision unit 10 updates the sample order with respect to the uploaded test results. That means that the decision unit 10 processes the test results, derives therefrom open and/or pending test requests, decides about further actions and initiates those actions, if necessary. Furthermore, the decision unit 10 updates the sample order stored within the database 11. The decision unit 10 can comprise a rule engine 12 by means of which that coordination functionality of the decision unit 10 can be supported. The rule engine 12 can be an off-the-shelf rule engine capable of handling facts and applying inference rules on those facts. The inference rules can be defined in advance and dynamically adapted to new circumstances.

The rule engine can add new or confirmation tests based on current test results, current test result flags, other sample information, such as sample quality, sample volume, sample turn around time, sample load balancing rules, previous sample results, etc., and/or patient related information, such as age, gender, location information, requester/ward, etc., or this test or any other requested test can be commented, blocked, released, replaced, modified or extended, e.g. by comments or flags.

The sample tube 50 is either immediately processed by the analytical unit 30 as indicated by backwardly directed arrow I, in case the analytical unit has the capabilities or the sample tube 50 is put back on one of the pre-analytical units 20 as indicated by backwardly directed arrow F.

The pre-analytical unit 20 is scanning the sample unit 50 again and sends the scan via link C to the decision unit 10. In case of still pending test requests, the decision unit 10 is downloading again the appropriate test request or target information via link C to the pre-analytical unit 20 and the described steps are repeated until all test requests/targets have been done and no open test request/target is existing.

Then, the sample tube 50 is sorted via link G into an archive tray by the at least one post-analytical unit 40, which is informed by the decision unit 10 via link H.

By means of the system 100, it is possible to realize that no special workflow logic has to be implemented into the host component 200. While links A, B, C, E and H describe communication links enabling the respective units to transfer information data among each other, for example by using appropriate interface protocols, respectively, links D, F, G and I correspond to transporting connections for the sample tube 50.

The host component 200 is relieved from any real-time duties as all required decisions, i.e. pre-analytical, analytical and post-analytical decisions are taken by the decision unit 10. High quality results can be delivered by proven process units within the system 100 and complex algorithms do not have to be implemented in the host component 200. The laboratory process as described above can be optimized by combining sample flow related decisions as pre-analytical, analytical and post-analytical steps with data management information as received test results optionally combined with available sample and patient information within the decision unit 10. Via standard host interface protocols, e.g. ASTM or HL7, those workflow and data management functions can be integrated fast, easy and with low risk into an existing laboratory environment. This reduces the complexity, improves laboratory quality and provides a satisfying work environment.

The system is scalable and extendable as pre-analytical, analytical and post-analytical units can be added based on the throughput and turn around time requirements. This can be done without change of the interface between the host component 200 and the decision unit 10.

It is possible to provide a plurality of pre-analytical units 20, wherein all of the pre-analytical units have the same functionality and perform the same task on a sample. Therefore, it is possible to handle a plurality of samples 1 to n in parallel. That means, for example, that samples 1 to i are handled by pre-analytical unit 20_1, whereas samples i+1 to n are handled by pre-analytical unit 20_2. This can be continued analogically in case of more than two pre-analytical units.

Alternatively, it is possible to provide a plurality of pre-analytical units 20, wherein each of the pre-analytical units can perform certain steps in the pre-analytical processing of a sample, thus the pre-analytical units complement one another with respect to the whole pre-analytical processing. That means, for example, in case of m steps which have to be done in the pre-analytical processing, that steps 1 to i are done for all samples by pre-analytical unit 20_1, whereas steps i+1 to m are performed by pre-analytical unit 20_2. The assignment of steps can be modified accordingly in case of more than two pre-analytical units.

Figure 2:
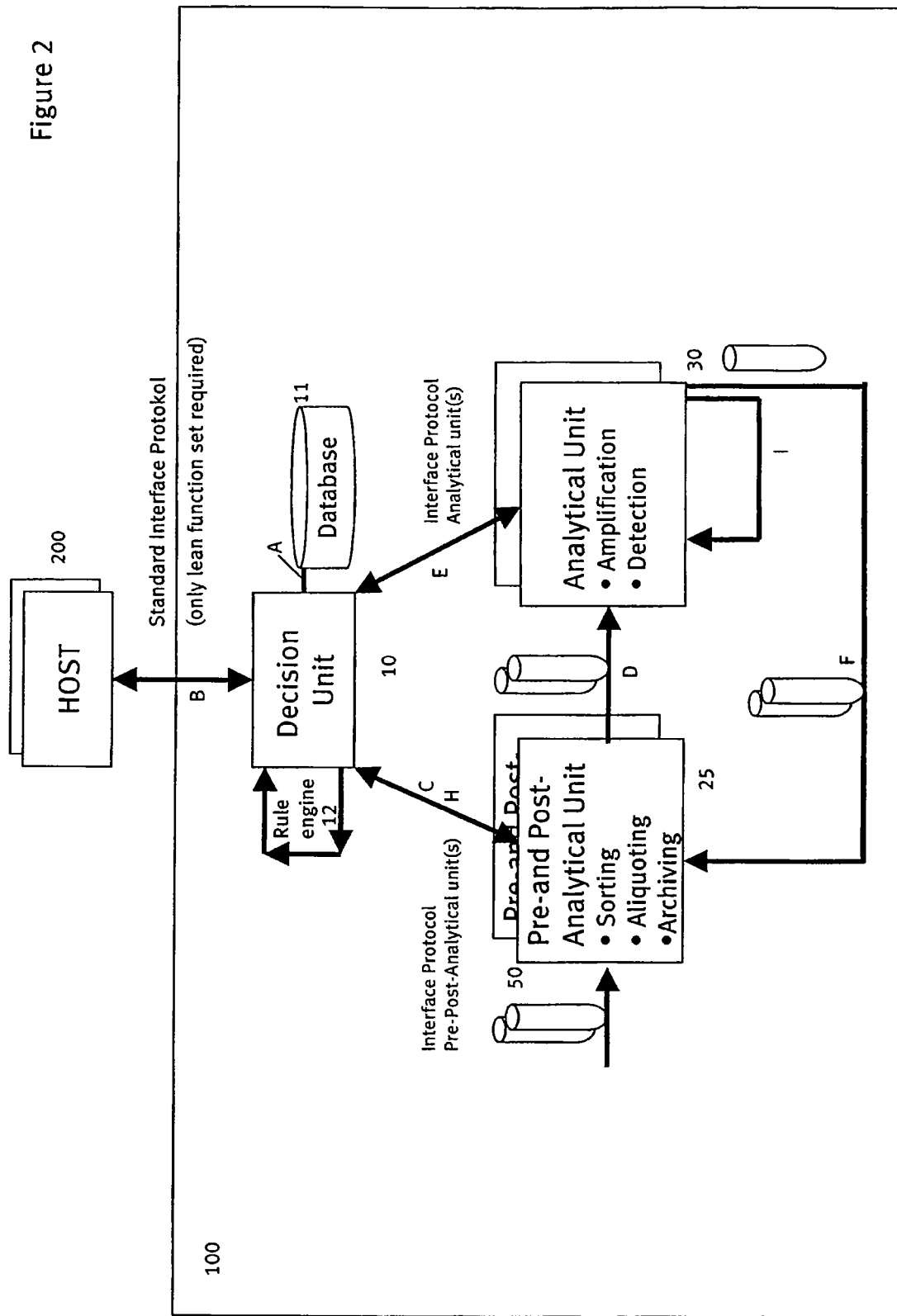
FIG. 2 shows a schematic block diagram of a further embodiment of a system according to the present disclosure.

FIG. 2 describes a further block diagram of an embodiment of the system according the present disclosure. The system 100 comprises a decision unit 10, at least one analytical unit 30 and at least one further unit 25 in which a pre-analytical unit and a post-analytical unit are combined. The decision unit 10 is again connected via a link A with a database 11 which can also be an integral part of the decision unit 10. The decision unit 10 can communicate with at least one host component 200 via a standard interface protocol, as indicated by link B. The decision unit 10 can also communicate with the pre- and post-analytical unit 25 and with the analytical unit 30 via appropriate interface protocols, respectively, as indicated by links C, E and H. As indicated on the left side a sample tube 50 is arriving in the pre- and post-analytical unit 25 where a sample scan is performed and sent to the decision unit 10. Based on the scan the decision unit 10 is downloading an appropriate sample order including a sample-ID and either the sample test request or target information, optionally combined with available sample and patient information, which is stored in the local database 11 of the decision unit 10. The stored sample order optionally combined with other information has been downloaded before from the host component 200 to the decision unit 10 of the system 100 via standard interface protocols.

Depending on the downloaded sample order/sample target information, the pre- and post analytical unit 25 is performing a required action, as for example sorting or aliquoting, and putting the sample tube 50 into an appropriate target. The sample order can be extended by the pre-analytic sorting/aliquoting information. Such extended sample order in terms of sample information, e.g. sample extension, sample position or any other information, is uploaded via link C from the pre- and post-analytical unit 25 to the decision unit 10. The sorted/aliquoted sample tube 50 is put via connection D on the analytical unit 30.

The analytical unit 30 is asking via link E for appropriate test request information from the decision unit 10. The analytical unit 30 is asking for such information either in batch mode or in query mode. The decision unit 10 is downloading the sample order or the extended sample order, which is to be understood in the broadest sense of sample information comprising the required information, to the analytical unit 30. After the required test has been done the test results are uploaded from the analytical unit 30 to the decision unit 10.

The decision unit 10 updates the sample order with respect to the uploaded test results. The decision unit 10 can add new or confirmation tests based on current test results, current test result flags, other sample information, such as sample quality, sample volume, sample turn around time, sample load balancing rules, previous sample results, etc., and/or patient related information, such as age, gender, location information, requester/ward, etc., or this test or any other requested test can be commented, blocked, released, replaced, modified or extended, e.g. by comments or flags. The sample tube 50 is either immediately processed by the analytical unit 30 as indicated by backwardly directed arrow I, in case the analytical unit has the capabilities, or the sample tube 50 is put back on the pre- and post-analytical unit 25 as indicated by backwardly directed arrow F. The pre- and post-analytical unit is scanning the sample tube 50 again and the scan is sent to the decision unit 10.

In case of still pending sample test requests, the before mentioned steps are repeated until all sample test requests have been done or no open target is existing on the sample tube 50. In case no open test requests are existing or no open target is existing, the sample tube 50 is sorted into an archive tray by the pre- and post analytical unit 25.

Figure 3:
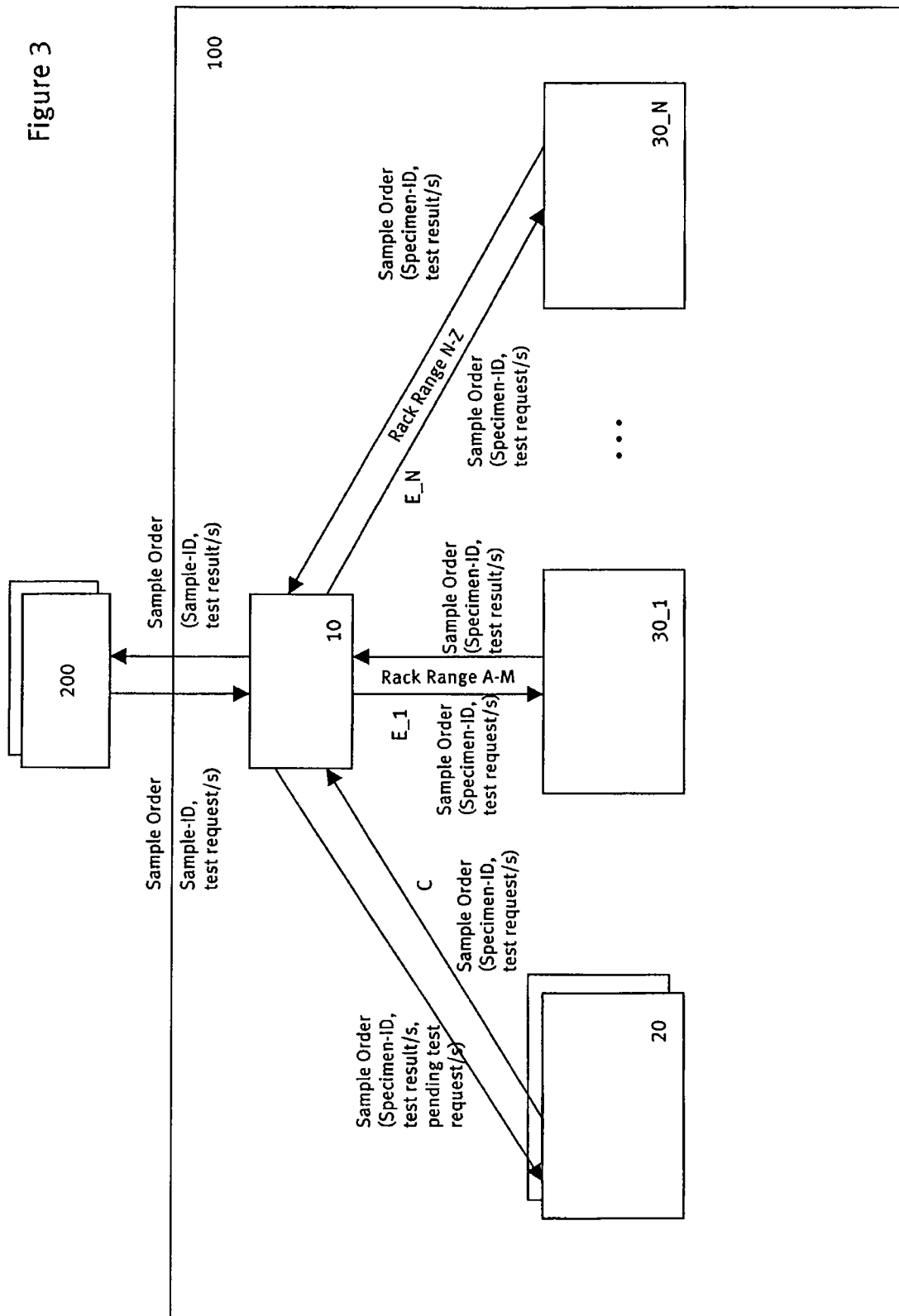
FIG. 3 shows a flowchart of an embodiment of the method according to the present disclosure.

FIG. 3 shows a flowchart of an embodiment of the method according to the present disclosure. The method as described hereinafter can be used in large molecular diagnostics sites. Those sites have typically one or more instruments for automated sample preparation and one or more automated amplification and detection instruments. Instruments for automated sample preparation are provided for example by COBAS AmpliPrep™ Instruments of Roche Diagnostics. As automated amplification and detection instruments COBAS TaqMan™ Analyser, COBAS TaqMan 48™ Analyser or COBAS Amplicor™ Analyser, all distributed by Roche Diagnostics, can be used. A number of the laboratories are using one or more so-called Hamilton Star™ for automated pipetting of primary sample tubes to so-called S-tubes of the mentioned COBAS AmpliPrep™ Instrument. These laboratories are running for example virology assays for HIV/HBV/HCV testing. The Hamilton system in a workflow as it is provided by an embodiment of the method according to the present disclosure can be used as an aliquot system generating out of a bar-coded primary sample tube an aliquot in a so-called SK 24 rack. The Hamilton system is not used as a pooling system. The decision unit as a part of an embodiment of the system according to the present disclosure manages the workflow described hereinafter and required data information transfer between the different units. The decision unit manages in a molecular diagnostics workflow an interface to a host component, a data flow between the so-called Hamilton system and any analytical unit, hereinafter called Amplilinkυ data stations, and collates test results with the corresponding sample tubes and reports sample and/or test order status towards a corresponding host component.

In the case described in FIG. 3, a sample order is generated in a host component 200. The sample order consists of a unique sample ID and a number of test requests. The sample order, namely the sample-ID and the test requests, is downloaded to the decision unit 10 as a part of a system 100. One or more pre-analytical units 20, which can be a Hamilton system, is sending a query to the decision unit 10 as soon as a sample tube has been scanned on the pre-analytical unit 20. The decision unit 10 is sending via link C the sample order, including a specimen-ID plus the sample test requests, to the pre-analytical unit 20. The pre-analytical unit 20 is processing the sample order. Depending on the test requests, sample material is pipetted in a rack, such as a SK-rack. The pre-analytical unit 20 is extending the sample order by the rack-ID and the rack-position. The extended sample order is uploaded via link C to the decision unit 10.

Alternatively, the sample order, that means the sample-ID plus the test requests, can also be entered directly into the pre-analytical unit 20, e.g. by loading the corresponding samples, assorted by test parameters. Therefore, the decision unit 10 must be able to handle unknown sample orders uploaded by the pre-analytical unit 20. The host component 200 must also be able to handle unknown samples, that means sample-ID plus sample test results, uploaded by the decision unit 10 at the end of the test process.

The decision unit 10 is receiving the extended sample order, namely the sample-ID, the sample-ID modified, the rack-ID, the rack-position and the test requests. The decision unit 10 is forwarding the sample order according to the rack-ID, received by the pre-analytical unit 20 and an assigned rack-range in case of multiple connections to appropriate analytical units 30 via respective links E_1, . . . , E_N. Those analytical units 30 can be assorted by rack-range as indicated by the numeration 30_1 to 30_N. In the case shown here, the analytical unit 30_1 handles rack range A to M, while the analytical unit 30_N handles rack range N-Z. The analytical unit 30_1 is processing the sample orders relating to rack ranges A to M. The analytical unit 30_N processes the sample orders relating to rack ranges N to Z. After having performed the corresponding tests, the respective analytical unit 30 is uploading via respective link E the sample order and the test results to the decision unit 10 including flags and comments. The decision unit 10 is updating the sample order with respect to the received test results. The decision unit 10 is uploading the updated sample order, including the test results to the host component 200. Such an upload can be performed according to predefined rules. The decision unit 10 can uploading the updated sample order periodically to the host component, thus informing the host component about the actual sample order/result status. Alternatively, the host component is only informed by a sample order upload when all test requests have been done. In case that there are still pending test requests, the decision unit 10 downloads again the sample order, including sample test results(s) and pending test request(s) via link C to the pre-analytical unit 20.

In the case shown here, racks must be pre-sorted by the laboratory, considering the target system the test requests are performed.

Figure 4:
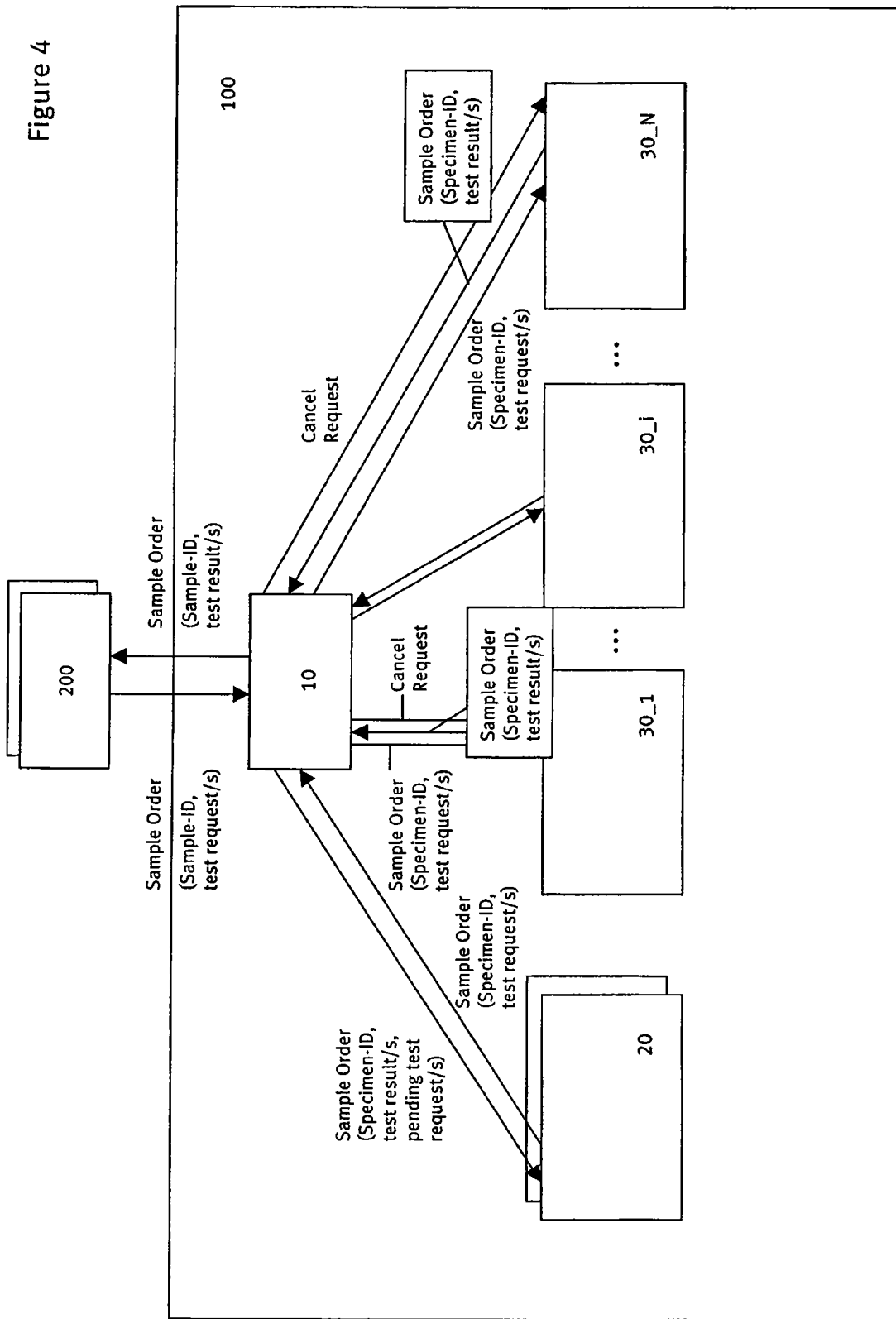
FIG. 4 shows a flowchart of a further embodiment of the method according to the present disclosure.

FIG. 4 shows a further flowchart of another embodiment of the method according to the present disclosure.

A sample order is again generated in a host component 200. The sample order consists of a unique sample-ID and a number of test requests to be made on the corresponding sample. The sample order, namely the sample-ID and the test requests, is downloaded to a decision unit 10, which is part of a system 100. One or more pre-analytical units 20, which is also included within system 100, is sending a query to the decision unit 10 as soon as the sample has been scanned on the pre-analytical unit 20. The decision unit 10 is sending via link C the sample order to the pre-analytical unit 20. The pre-analytical unit 20 is processing the sample order. Depending on the test requests, sample material is pipetted in an appropriate rack, which can be for example a so-called SK-24 rack. The pre-analytical unit 20 is extending the sample order by a rack-ID and a rack-position. The extended sample order is uploaded via link C to the decision unit 10.

As already mentioned in connection with FIG. 3, sample orders can also be entered directly on the pre-analytical unit 20, e.g. by loading samples, assorted by test parameters. Therefore, the decision unit 10, as well as the host component 200, must be able to handle unknown sample orders uploaded by the pre-analytical unit 20 and the decision unit 10, respectively.

The decision unit 10 is receiving the extended sample order, including the sample-ID, a sample-ID modified, a rack-ID, a rack-position and test requests. The decision unit 10 is forwarding via batch download the sample order to all analytical units 30_1, . . . , 30_N, which are connected with the decision unit 10 via links E_1, . . . , E_N, respectively. The respective analytical unit 30_i among the plurality of analytical units 30, which is receiving the SK-24 rack is processing the sample order. This analytical unit 30_i is uploading the sample order and the test results to the decision unit 10, including flags and comments. After the decision unit 10 has received the complete sample, the decision unit is sending a cancel request via respective links E_j to the other analytical units 30_j (i≠j) to delete an appropriate order automatically out of a local analytical data base. The decision unit 10 is updating the sample order with respect to the test results and uploading the updated sample order including the test results to the at least one host component 200. In case that there are still pending test requests, the decision unit 10 downloads again the sample order, including sample test results(s) and pending test request(s) via link C to the pre-analytical unit 20.

In the case shown here, no rack pre-sorting is required, contrary to the scenario shown in connection with FIG. 3. Overlapping test panes in case of multi analytical unit connections are supported.

FIG. 5 shows a recursive workflow which can be realized within an embodiment of the system according to the present disclosure. A simple recursive workflow, based on test requests only, is implemented between a pre-analytical unit, herein after called Hamilton, a decision unit, called PSM, and an analytical unit, called Amplilink. Such a recursive workflow means, in the example shown here, that only the remaining test requests, which have not been processed up to now, are considered. If all tests have been done an appropriate flag is sent to the pre-analytical unit, acting as a sample preparation unit. Optionally completely processed samples can then go into archive. In case that the requested sample is not known by the decision unit, an appropriate flag is sent to the pre-analytical unit.

The example shown in FIG. 5 describes a sample "123" with test requests "T1/T2/T3/T4". The at least one pre-analytical unit Hamilton asks via query 1 the decision unit PSM for sample "123". As an answer, which is sent from the decision unit PSM to the pre-analytical unit Hamilton, a sample-ID "123" with test requests "T1/T2/T3/T4" is provided. The pre-analytical Hamilton performs pre-analytical actions, e.g. pipetting, and sends the result back to the decision unit PSM for sample "123", which reads "sample-ID 123 T1; R-ID/R-Pos/123". In reaction to such a result, the sample is forwarded to an appropriate analytical unit for processing test request T1. Via a query 2, the at least one pre-analytical unit Hamilton asks the decision unit PSM for sample "123". As an answer, the decision unit PSM sends to the pre-analytical unit Hamilton where the sample is put on the sample-ID "123" with test requests "T2/T3/T4", since T1 has been already processed successfully. As a result, the pre-analytical unit Hamilton where the sample is put on performs the pre-analytical action (pipetting) and sends the result back to the decision unit PSM, which reads the "sample-ID 123 T2; R-ID/R-Pos/123". In reaction of such a result, the sample "123" is forwarded by the decision unit PSM to an appropriate analytical unit, which processes test request T2. After that, the at least one pre-analytical unit Hamilton asks again via query 3 the decision unit PSM for sample "123". The decision unit PSM answers by providing the sample-ID "123" with test request "T3/T4". The pre-analytical Hamilton where the sample is put on makes pipetting for sample "123" and sends the results back to the decision unit PSM, which reads "sample-ID 123 T3, T4; R-ID/R-Pos/123". Therefore, the sample is forwarded to an analytical unit, which is capable of processing test requests T3, T4. After that, the sample is forwarded back to the at least one pre-analytical unit Hamilton, which asks via query 4 the decision unit PSM again for sample "123". The decision unit provides the pre-analytical unit with information of the sample "123", namely the sample-ID "123", with no test requests left. That means, that in this case, an empty record is sent back, so that the pre-analytical unit Hamilton does not perform any further action. The sample can then be forwarded to a post-analytical unit in which the sample can be archived. Such a post-analytical unit can be consolidated with a pre-analytical unit within a common physical device.

According to one embodiment, a system for managing information relating to requests for a number of tests to be made on at least one sample 50 within a laboratory environment is disclosed. The system comprises at least one pre-analytical unit 20 configured to scan the at least one sample 50 and to sort, aliquot and/or archive the at least one sample 50 on request according to respective test requirements included within a respective sample order, at least one analytical unit 30 configured to run at least one test of the number of tests on the appropriately sorted and/or aliquoted sample 50, and a decision unit 10 enabling at least one host component 200 to access the system and to submit the sample order for the at least one sample, and acting as intermediary and coordinator in communication between the at least one pre-analytical unit 20 and the at least one analytical unit 30 such that the number of tests can be performed via a recursive workflow until a pre-given stopping criterion is fulfilled, the decision unit 10 being further configured to collate gained test results appropriately with the sample 50 and to give a respective report towards the at least one host component 200.

The system can also comprise in another embodiment at least one sample reception unit configured to receive the at least one sample.

In a further embodiment, a decision unit 10 for managing information in real-time relating to requests for a number of tests to be made on at least one sample 50 in a system within a laboratory environment is disclosed. The laboratory environment comprising at least one pre-analytical unit 20 and at least one analytical unit 30, wherein the decision unit 10 enables at least one host component to access the system and to submit a sample order for the at least one sample, and acts as intermediary and coordinator in communication between the pre-analytical unit 20 and the analytical unit 30 such that the number of tests can be performed via a recursive workflow, coordinated by the decision unit 10 until a pre-given stopping criterion is fulfilled, the decision unit 10 being further configured to collate gained test results appropriately with the sample 50 and to give a respective report towards the at least one host component 200.

The decision unit 10 in one embodiment is combining the information coming from the different units, e.g. from the at least one pre-analytical unit 20 and the at least one analytical unit 30, as a basis to make a next decision.

The decision unit 10 itself in one embodiment can be configured to optionally combine current analytical data, such as current analytical test result information with other sample related information to decide the next pre-analytical step. Sample related information is to be understood within the scope of the present specification in a broad sense, including sample specific information, such as sample quality, sample volume, sample turn around time, sample load balancing information, delta checks with previous results, and/or patient related demographic information, such as age, gender, location information, requester/ward etc.

A further embodiment refers to a method for managing information relating to requests for a number of tests to be made on at least one sample within a laboratory environment, the laboratory environment comprising at least one pre-analytical unit 20, at least one analytical unit 30 and a decision unit 10. The method comprises: receiving the sample, transporting the sample to the at least one pre-analytical unit 20, identifying the sample and assigning the sample to a sample order, processing the sample according to the sample order by a dynamically adaptable coordinated interaction of the at least one pre-analytical unit 20 and the at least one analytical unit 30, and giving a report about the processing to at least one host component 200, wherein the coordination between the at least one pre-analytical unit 20 and the at least one analytical unit 30 is managed by the decision unit 10 acting as intermediary and coordinator in communication between the respective units and the report is given by the decision unit 10 acting as consolidating front end related to the at least one host component 200.

The processing in one embodiment can be done via a recursive workflow.

In another embodiment, the recursive workflow comprises: processing the sample order by the at least one pre-analytical unit by sorting and/or aliquoting the sample and putting the sample into an appropriate target, putting the sorted and/or aliquoted sample on the at least one analytical unit, depending on the sample order with the sample test request information and the sample related information, downloaded from the decision unit to the analytical unit, performing at least one appropriate test among the number of tests by the analytical unit, uploading the test results from the analytical unit to the decision unit, updating the sample order with respect to the uploaded test results at the decision unit, and repeating at least some of the steps until a pre-given stopping criterion is fulfilled.

When a test is performed, the test results are sent back to the decision unit. At the decision unit, the sample order is accordingly updated with respect to the uploaded test results, i.e. by current test result information and with respect to further current sample related information. The test result information can comprise all still open or pending test requests in one embodiment. The further current sample related information can comprise any information describing situational interests in another embodiment. Optionally, new tests or confirmation tests can be generated by the decision unit based on current test results, current result flags, previous sample results, any other patient related demographic information, such as gender, age, requester, etc. or the test just made or any other requested test can be commented, blocked, released, replaced, modified or extended, e.g. with comments or flags. Failed tests which have to be repeated can also be included in another embodiment. The updated sample order is processed again until a pre-given stopping criterion is reached. Such a stopping criterion can be fulfilled, e.g. when all test requests have been done in one embodiment.

One embodiment of the method further comprises receiving the sample order comprising a sample-ID and the sample test requests with sample test request information and sample related information from the at least one host component. That means that the sample order comprising the sample-ID and the test requests is downloaded from the at least one host component to the decision unit. In that case, it is conceivable, that the pre-analytical unit is sending a query to the decision unit after the sample received at the pre-analytical unit has been scanned. The decision unit sends the sample order to the pre-analytical unit. The pre-analytical unit processes the sample order by sorting and/or aliquoting the sample, depending on the sample test request information, and by putting the sample as a sample tube into an appropriate target. It is possible, for example, that depending on the sample test request information sample material is pipetted into an appropriate secondary tube which is assigned to an appropriate rack and target.

Alternatively, in another embodiment, it is also possible that the sample order is directly received by the pre-analytical unit. That means that the sample order can be directly entered on the pre-analytical unit, e.g. by loading sample tubes assorted by test parameters. In that case the decision unit must be able to handle unknown sample orders uploaded by the pre-analytical unit.

According to one embodiment, the system further comprises at least one post-analytical unit, configured to archive measured samples. The post-analytical unit is an equipment used to perform post-analytical functions in a respective laboratory, as for example archiving of samples. The equipment in one embodiment can be a robot system doing the required post-analytical steps.

It is also possible, that the post- and the pre-analytical units in one embodiment are consolidated within one common physical equipment.

The decision unit according to another embodiment provides one consolidating and standardized front end for all pre-analytical, analytical and post-analytical units of the system related to one or more existing host systems. Those host systems are relieved from real-time duties.

The system according to another embodiment provides one backbone to realize advanced sample workflows, thus increasing laboratory efficiency and delivering high quality results. The system allows to combine pre-analytical, analytical and post-analytical decisions with data management functions as automatic result validation rules. This is, as already mentioned above, a pre-requisite for optimizing the complete laboratory process.

It is possible within a further embodiment of the system that the system can communicate with at least one host component via any standard host interface protocol, such as via ASTM or HL7. Via such standard host interface protocols, and a standard function set, the system can be integrated fast, easy and with low risk within a specific laboratory environment. This reduces complexity and improves quality.

According to another embodiment of the system, the decision unit acts as a distributor unit, distributing the at least one sample to the at least one analytical unit according to distribution criteria, which have been configured by the decision unit itself executed in real-time, based on pre-analytical information from the at least one pre-analytical unit and/or on current analytical data which are optionally combined in real-time with current result flags, other sample information, such as sample quality, sample volume, sample turn around time, sample load balancing rules, previous sample results, etc. and/or patient related information such as age, gender, location information, requester/ward, patient demographic data, etc. Moreover, a current test or any other requested test can be commented, blocked, released or replaced, modified or extended, e.g. with comments or flags. Current analytical data means those data which can be derived from already performed tests and corresponding test results.

Generally, it is possible that in one embodiment the system comprises a plurality of analytical units, enabling the system to run a plurality of tests. Those tests can be performed in parallel. Furthermore, those tests can differ from each other. That means that the number of tests to be made on the at least one sample can be run by different suitable analytical units, even in parallel, if necessary.

In a further possible embodiment of the system, the at least one pre-analytical unit is further configured to put the sorted and/or aliquoted sample into an appropriate target for transfer to the at least one analytical unit.

It is also possible in another embodiment, that the analytical unit is configured to receive open test requests either in query mode or in batch mode from the decision unit.

One of the major characteristics of the recursive workflow, which can be realized by the system according to one embodiment, is that any next action to be done with the at least one sample, is taken at one logical point. This logical point is realized by the decision unit which is typically located in a so-called sample distribution area of the laboratory. The action itself can be a sorting step, an aliquoting step, a combined sorting and aliquoting step or an archive step. Any execution of a pre-analytical action is either automated by a robot system or semi-automated by a computer aided manual system.

The decision unit in one embodiment can encompass or be connected with a rule engine.

The major steps of a recursive workflow, as it can be provided by an embodiment of the system according to the present disclosure, can be described as follows:

1. The at least one sample is arriving in a sample reception unit and transported manually or automatically to a so-called sample distribution area, which includes the at least one pre-analytical unit and the decision unit.

2. In the at least one pre-analytical unit, the sample, which generally can be identified by a barcode, is scanned either on a manual scanner in case of a manual scan place, or by a scanner in a robot system.

3. The decision unit checks, if the sample-ID, indicated by the barcode, is known. In case that the sample is known and there are still open requests, which can be derived from a sample order, which has been received by the system and stored accordingly in a database connected with the decision unit, the sample is distributed to an appropriate next target. The distribution criteria itself have been configured, as already indicated, in the decision unit. Pre-analytical information and current analytical data can be considered in such a decision process. Optionally, new tests or confirmation tests can be generated by the decision unit based on current test results, current result flags, previous sample results, any other patient related demographic information, such as gender, age, zip-code, requester, etc. or the test just made or any other requested test can be commented, blocked, released, replaced, modified or extended, e.g. by comments or flags.

4. The sample is then transported manually or automatically on an appropriate tray or rack. The tray or rack is transported manually or automatically from the sample distribution area to a corresponding analytical unit, which is able to perform the required measurement.

5. The sample is put on the analytical unit. The analytical unit is receiving the open requests included in the sample order either in query or in batch mode from the decision unit.

6. Finally the test result from each test is uploaded to the decision unit.

7. The decision unit is updating the sample order by current test result information. Optionally, new tests or confirmation tests can be generated in real-time by the decision unit based on current test results, current result flags, previous sample results, any other patient related demographic information, such as gender, age, zip-code, requester, etc. or the test just made or any other requested test can be commented, blocked, released, replaced, modified or extended, e.g. by comments or flags.

8. The sample is either immediately processed on the analytical unit, in case the analytical unit has the capabilities, or transported back to the pre-analytical unit.

9. The sample is scanned again and, in case that there are still open test requests, appropriately distributed to a further target.

10. In case that there are no open test requests left, the completely measured sample can be archived by a post-analytical unit.

Such a recursive workflow, which can be performed in one embodiment by means of a system according to the present disclosure and/or by means of a decision unit according to the present disclosure, delivers a lot of advantages, some of which are summarized in the following.

The process is clear, since all sample distribution decisions are taken by the decision unit. The decision taken by the decision unit considers pre-analytical information as well as current analytical test results, if already available. Optional available sample information of patient related information can be considered. The recursive workflow realizes a combination of pre-analytical rule settings with analytical results, optionally combined with other sample and patient related information which represent laboratory processes. The samples remain in the laboratory until all required actions have been done. Furthermore, the process to be executed is easy to learn for any laboratory worker due to a clear process structure. Moreover, a fully computer aided decision process and paperless working is decreasing the error rate and increasing the quality.

The present disclosure in other embodiments further refers to a computer program product with a computer-readable medium and a computer program stored on the computer-readable medium with a program code which is suitable for carrying out a method according to an embodiment of the present disclosure when the computer program is run on a computer, such as on a computer which is incorporated within a system according to an embodiment of the present disclosure.

The present disclosure in still other embodiments also refers to a computer program with a program code which is suitable for carrying out a method according to an embodiment of the disclosure when the computer program is run on a computer, such as on a computer which is incorporated within a system according to an embodiment of the present disclosure.

What is claimed is:

1. A method for realizing a workflow for performing a number of tests to be made on at least one sample in a system within a laboratory environment, the system comprising:

a decision unit comprising a processor, a memory coupled to the processor, and tangible media containing non-transitory machine readable instructions stored in the memory;

at least one pre-analytical unit being configured to receive and to scan the at least one sample and to sort, aliquot and/or archive the at least one sample on request according to respective test requests included within a respective sample order comprising a sample-ID and sample test requests, wherein pre-analytical sorting/aliquoting information is uploaded from the pre-analytical unit to the decision unit and to scan the at least one sample again when the sample is transported back to the pre-analytical unit after the sample order has been updated by the decision unit; and a plurality of analytical units, each being configured to run at least one test of the number of tests on the appropriately sorted and/or aliquoted sample and to upload the test results to the decision unit, the decision unit enabling at least one host to access the system and to submit the sample order for the at least one sample, and acting as intermediary and coordinator in communication between the at least one pre-analytical unit and the plurality of analytical units, wherein the decision unit coordinates processing of the number of tests via a workflow until all tests have been done, the decision unit being further configured to:

download the sample order comprising the sample-ID and sample test requests from the at least one host, to distribute the at least one sample to an appropriate analytical unit according to distribution criteria which are configured by the decision unit itself and which are based on pre-analytical information from the at least one pre-analytical unit and on test results from tests of the number of tests which have already been performed by at least one analytical unit combined with other sample related information, to update the sample order with respect to the uploaded test results and to add new or confirmation tests and to comment, block, release, replace, modify or extend any requested test and to combine current analytical data with other sample related information to decide a next pre-analytical step, so that the updated sample order is to be processed again until all test requests have been done, to collate gained test results with the sample, and to give a respective report towards the at least one host;

the method comprising the following steps:

A. receiving the sample by the at least one sample reception unit,

B. transporting the sample to the at least one pre-analytical unit,

C. identifying the sample by the of least one pre-analytical unit and assigning the sample to a sample order by the decision unit, D. performing a sample scan by the at least one pre-analytical unit and sending the sample scan to the decision unit, E. receiving by the decision unit the sample order comprising a sample-ID and the sample test requests with sample test request information and sample related information from at least one host,
F. processing the sample according to the sample order by a dynamically adaptable coordinated interaction of the at least one pre-analytical unit and the plurality of analytical units, wherein the at least one sample is distributed to an appropriate analytical unit according to distribution criteria which are configured by the decision unit itself and which are based on pre-analytical information from the at least one pre-analytical unit and on test results from tests of the number of tests which have already been performed by at least one analytical unit optionally combined with other sample related information, and wherein the sample order is updated with respect to uploaded test results,
  F' in response to any requested test by the decision unit, commenting, blocking, releasing, replacing, modifying or extending such test,
  F'' combining, by the decision unit, current analytical data with other sample related information to decide a next pre-analytical step, so that the updated sample order is to be processed again until all test requests have been done,
  F''' scanning the at least one sample again, by the at least one pre-analytics unit, when the sample is transported back to the pre-analytical unit after the sample order has been updated by the decision unit, and
  F'''' appropriately distributing by the decision unit, the sample to a further target in case that there are still open test requests,
G. collating, by the decision unit, gained test results with the corresponding sample, and
H. giving, by the decision unit, a report about the processing to the at least one host, wherein the coordination between the at least one pre-analytical unit and the plurality of analytical units is coordinated by the decision unit acting as intermediary and coordinator in communication between the respective units and the report is given by the decision unit to the at least one host.

2. The method according to claim 1, wherein step F comprises the following sub-steps:
  F_1. processing the sample order by the pre-analytical unit by sorting and/or aliquoting the sample and putting the sample into an appropriate target,
  F_2. putting the sorted and/or aliquoted sample on an appropriate analytical unit,
  F_3. depending on the sample order with sample test request information and sample related information, downloaded from the decision unit to the plurality of analytical units, performing at least one appropriate test among the number of tests by at least one of the plurality of analytical units,
  F_4. uploading the test results from the at least one of the plurality of analytical units to the decision unit,
  F_5. updating the sample order with respect to the uploaded test results at the decision unit, and
  F_6. repeating at least some of the steps until a pre-given stopping criterion is fulfilled.

3. The method according to claim 1, further comprising the step of sorting the sample into an archive tray in case that all test requests have been done.

4. The method according to claim 1, wherein the report given towards the at least one host comprises test results and/or a sample order status.

* * * * *